United States Patent [19]

Kaplan et al.

[11] Patent Number: 5,034,397

[45] Date of Patent: Jul. 23, 1991

[54] STABLE, WATER SOLUBLE SALT COMPOSITIONS OF M-AMSA IN 1-METHYL-2-PYRROLIDINONE

[75] Inventors: Murray A. Kaplan, Syracuse; Robert A. Lipper, Manlius, both of N.Y.

[73] Assignee: Bristol-Myers Squibb Co., New York, N.Y.

[21] Appl. No.: 808,202

[22] Filed: Dec. 12, 1985

[51] Int. Cl.$^5$ .............................................. A61K 31/44
[52] U.S. Cl. ................................................... 514/297
[58] Field of Search ......................................... 514/297

[56] References Cited

U.S. PATENT DOCUMENTS 4,425,348 1/1984 Kaplan et al. .......................... 514/297
4,575,509 3/1986 Chen et al. ............................. 514/297

Primary Examiner—Jerome D. Goldberg
Attorney, Agent, or Firm—Sandra M. Nolan

[57] ABSTRACT

This invention relates to novel compositions of the antitumor agent [4'-9-(acridinylamino) methanesulfon-m-anisidide], (m-AMSA). Acid salts of m-AMSA are dissolved in 1-methyl-2-pyrrolidinone to provide highly stable solutions. The solutions may be diluted with Sterile Water for Injection, U.S.P. to provide stable, non-precipitating solutions for intravenous use.

11 Claims, No Drawings

STABLE, WATER SOLUBLE SALT COMPOSITIONS OF M-AMSA IN 1-METHYL-2-PYRROLIDINONE

BACKGROUND OF THE INVENTION

1. Field of the Invention

The novel compositions of the present invention possess the advantageous pharmacological properties of the known free-base compound and in addition have unexpectedly high water-solubility, thus allowing preparation of useful dosage forms for intravenous administration.

2. Description of the Prior Art

The acridine derivative m-AMSA [4'9-(acridinylamino) methanesulfon-m-anisidide] has been reported by Cain, et al. in Europ. J. Cancer 10:539-549 (1974) to possess significant antitumor activity in animal tumor systems.

When an antitumor agent such as m-AMSA is employed for pharmaceutical use, it is recognized that solubility of the agent is often the controlling factor in determining route of administration and dosage forms. For instance, a water-soluble substance can be generally administered intravenously whereas a water-insoluble material is limited to other forms of parenteral administration such as intramuscular and subcutaneous. A therapeutic agent having water solubility also facilitates preparation of oral and non-intravenous parenteral dosage forms. Thus, it is decidedly advantageous if a therapeutic agent is water-soluble, particularly when one considers that the most direct route for achieving therapeutic blood levels of a drug is by intravenous administration.

The free-base form of m-AMSA has very limited solubility in water and thus cannot be used as a dosage form for intravenous administration. Attempts have been made to prepare acid addition salts to overcome this solubility problem, but the reported monohydrochloride and monomethanesulfonate salts also proved insufficiently water-soluble.

The use of various m-AMSA salts has been previously reported. U.S. Pat. No. 4,335,244 discloses the use of m-AMSA lactate hemiacetonate. U.S. Pat. No. 4,322,424 discloses the use of m-AMSA gluconate salts. European Patent No. 0 035 862 further discloses the use of the galacturonic, glucose-6-phosphate, gluconic, ascorbic, b-glycerophosphoric, glucuronic, glyceric, citric, acetic, propionic, gallic, isethionic, malonic, D,L-malic, succinic, d-tartaric, glutaric, mucic, phosphoric, salicylic, glycolic, benzoic, methanesulfonic,. gentisic, sulfuric, nitric and sulfamic salts of m-AMSA. However, while the salts disclosed are reported to be efficacious in varying degrees, they all have relatively low solubilities, i.e. less than 5-15 mg/ml of m-AMSA activity in the solvents employed, e.g. water, dimethylformamide, dimethylacetamide, methanol, anhydrous ethanol, isopropanol or combinations thereof.

The m-AMSA formulation presently in clinical use consists of two sterile liquids combined just prior to use. A solution of m-AMSA in anhydrous N,N-dimethylacetamide is contained in an ampule. A separate vial contains an aqueous L(+)-lactic acid solution for use as a diluent. When mixed, the resulting m-AMSA solution is administered by i.v. infusion.

While the present clinical formulation provides an intravenous dosage form, it suffers from several disadvantages. In addition to the obvious difficulties in preparing and administering the dosage form, it contains dimethylacetamide as a vehicle. Dimethylacetamide has been reported to show various toxic symptoms in animals and may thus prove to be unacceptable or undesirable as a pharmaceutical vehicle.

It is accordingly an object of the present invention to provide water-soluble, stable, therapeutically acceptable forms of m-AMSA which can be administered intravenously (as well as by other routes) and which do not contain or require dimethylacetamide as a pharmaceutical vehicle. This object as well as other features and advantages of the invention will be readily apparent to those skilled in the art from the disclosure set out below.

SUMMARY OF THE INVENTION

The present invention provides stable, solutions of m-AMSA salts at concentrations substantially higher than are obtainable with aqueous solvents, i.e. 100–200 mg/ml and preferably 50–100 mg/ml. Such solutions are prepared by dissolving acid salts of m-AMSA in 1-methyl-2-pyrrolidinone or preparing such acid salts in situ in 1-methyl-2-pyrrolidinone.

DETAILED DESCRIPTION

The m-AMSA acid-salt solvent of the present invention, 1-methyl-2-pyrrolidinone, is a relatively non-toxic chemical, used as a solvent for polymers, chlordane, DDT, sorbitol, sugars and numerous other materials. It is miscible with water, ethanol, ether, chloroform, benzene, ethyl acetate and carbon disulfide.

Many conventional pharmaceutically acceptable acid addition salts of m-AMSA are only slightly soluble in water and are thus unsuited for preparation of aqueous intravenous solutions. This is evident from literature references to the hydrochloride and methanesulfonate salts as well as from solubility tests carried out by the present inventors and others on salts such as levulinate, citrate, gluconate, tartrate, acetate, lactobionate and the like.

An investigation of the solubility properties of the acid-salt of m-AMSA employed with solvents used in the prior art indicates that aqueous solutions of m-AMSA greater than 15 mg/ml are not disclosed in the prior art.

While such solubility is adequate for most purposes, it has now been discovered that substantially higher concentrations of a stable solution may be obtained when as much as 100 to 200 mg/ml and preferably 50 to 100 mg/ml of an acid-salt of m-AMSA is dissolved in 1-methyl-2-pyrrolidinone. The composition containing an m-AMSA acid-salt in 1-methyl-2-pyrrolidinone is prepared by mixing the m-AMSA acid-salt and 1-methyl-2-pyrrolidinone to provide 20 to 200 mg/ml of m-AMSA activity. A preferred embodiment comprises a mixture of about 50 to 100 mg/ml of m-AMSA activity. Preparation of the water-soluble compositions of the present invention may be accomplished by simply mixing the appropriate quantity of the concentrate of m-AMSA acid-salt and 1-methyl-2-pyrrolidinone with water in the proper proportions or preparing such acid-salts in situ in 1-methyl-2-pyrrolidinone.

For preparation of unit dosage forms of the present compositions, the m-AMSA base may be used in any therapeutically effective dose. In the treatment of mammalian tumors, the salts and compositions of the present invention may be administered either orally or parenterally, but preferably in dosages (adjusted for the amount of the m-AMSA base) and according to regimens previously disclosed in the literature. A suggested dosage range of m-AMSA base in a unit dosage form is from about 20 to 100 milligrams.

The compositions provided by the present invention exhibit substantially the same pharmacological properties as the prior art m-AMSA forms. Because of their water-solubility, however, they may be used to prepare dosage forms for intravenous administration which do not contain an undesirable pharmaceutical vehicle such as dimethylacetamide. Furthermore, because of their unusually good stability in solution the compositions may be used to prepare a product for dilution with sterile water or a sterile aqueous vehicle as a parenteral dosage form.

The compositions of the present invention may be used to prepare oral or non-intravenous parenteral dosage forms as well as the preferred intravenous injectable product. The compositions have acceptable stability in aqueous solution, to permit administration of an effective dose of m-AMSA in a relatively small volume of parenteral solution.

The compositions of the present invention may be administered either orally or parenterally, but preferably parenterally, in dosages (adjusted for amount of m-AMSA activity) and according to regimens previously disclosed in the literature. Particularly preferred dosage forms may be provided by diluting 1-methyl-2-pyrrolidinone/m-AMSA acid-salt solutions at concentrations of 20, 50 and 100 mg/ml m-AMSA activity with equal volumes or more of Sterile Water for Injection, USP to provide highly stable solutions of 1 to 50 mg/ml of m-AMSA which are stable without precipitation, even after standing, shaking or stirring for at least one week at 25° C. No significant activity loss is noted in the diluted solutions for at least one month at 25° C.

Concentrated solutions of m-AMSA-L(+)-lactate or pyroglutamate salts and 1-methyl-2-pyrrolidinone will provide at least a 100–200 mg/ml m-AMSA solution which will not precipitate. A particularly desirable feature of the present invention is that the resulting solution demonstrates no observable precipitation for at least one year at temperatures of 25° C. at concentrations of 20 to 100 mg/ml m-AMSA activity and demonstrate less than 10% activity loss during such time.

Table 1 sets forth the results of a series of storage studies which demonstrate the stability of lactic acid and pyroglutamic acid-salts of m-AMSA in 1-methyl-2-pyrrolidinone.

TABLE 1

Stability of m-AMSA in 1-methyl-2-pyrrolidinone

| Conc. of m-AMSA in mg/ml | Molar Equivilent of Acid | % Loss | | | | | | | | | |
|---|---|---|---|---|---|---|---|---|---|---|---|
| | | 100° C. | 56° C. | | | | 45° C. | | | 37° C. | |
| | | 1-D | 1-W | 2-W | 1-M | 5-M | 2-W | 1-M | 5-M | 1-M | 2-M |
| 30 | 2-(LA) | | 6.4 | 7.6 | 6.7 | | 0.6 | 6.8 | | 3.4 | 0 |
| 50 | 2-(LA) | 11.1 | | | | 39.0 | | | 12.1 | | |
| 50 | 1-(LA) 1-D, L-PGA | 5.9 | | | | 21.0 | | | 6.0 | | |
| 50 | 2-D, L-PGA | 1.5 | | | | 13.2 | | | 0 | | |
| 100 | 1-(LA) 1-L-PGA | 11.4 | | | | | | | | | |
| 100 | 2-L-PGA | 5.6 | | | | | | | | | |
| 100 | 1-L-PGA | 3.7 | | | | | | | | | |

| Conc. of m-AMSA in mg/ml | Molar Equivilent of Acid | % Loss | | | | | | | | |
|---|---|---|---|---|---|---|---|---|---|---|
| | | 37° C. | | | | | | 25° C. | | |
| | | 3-M | 4-M | 5-M | 9-M | 14-M | 14-M* | 14-M | 16-M | 30-M |
| 30 | 2-(LA) | 0.8 | 4.4 | | | | | 5.5 | 6.2 | 9.4 |
| 50 | 2-(LA) | | | 0 | 1.0 | | | 0 | | |
| 50 | 1-(LA) 1-D, L-PGA | | | 0 | 0 | | | 0 | | |
| 50 | 2-D, L-PGA | | | 0 | 0 | | | 0 | | |
| 100 | 1-(LA) 1-L-PGA | | | | | 15.3 | 3.1 | 0 | | |
| 100 | 2-L-PGA | | | | | 8.0 | 5.3 | 0 | | |
| 100 | 1-L-PGA | | | | | 3.4 | 2.4 | 0 | | |

Legend:
L(−)-Lactic Acid = (LA)
Pyroglutamic Acid = PGA
Days = D
Weeks = W
Months = M
* = High Intensity Light (400 foot-candles)

The following examples are given in illustration of, but not in limitation of, the present invention.

EXAMPLE 1

An m-AMSA-L(+)-lactate salt dosage form of the present invention was prepared by the following procedure:

Ten grams of m-AMSA base was dissolved in 85 ml of 1-methyl-2-pyrrolidinone by rapid stirring.

One molar equivalent of L(+)-lactic acid (2.29 g), was then added and rapid stirring was continued to dissolve the lactic acid. The volume was then brought up to 100 ml with 1-methyl-2-pyrrolidinone and rapidly stirred for an additional ½ hour. The resulting solution contained 100 mg/ml of m-AMSA activity.

The solution was passed under a nitrogen atmosphere through a 0.22 micron pore size membrane filter using aseptic technique and the filtrate collected in a suitable sterile container.

Five ml portions of filtrate were placed in 8.5 cc sterile flint glass vials and the vials stoppered with rubber closures and sealed with aluminum shells.

EXAMPLE 2

An m-AMSA-L(+)-lactate salt dosage form of the present invention was prepared by the following procedure:

Ten grams of m-AMSA base was dissolved in 85 ml of 1-methyl-2-pyrrolidinone by rapid stirring.

Two molar equivalents of L(+)-lactic acid (4.58 g), was then added and rapid stirring continued to dissolve the lactic acid. The volume was then brought up to 100 ml with 1-methyl-2-pyrrolidinone and rapidly stirred for an additional ½ hour. The resulting solution contained 100 mg/ml of m-AMSA activity.

The solution was passed under a nitrogen atmosphere through a 0.22 micron pore size membrane filter using aseptic technique and the filtrate collected in a suitable sterile container.

Five - 15 ml portions of filtrate were placed in 17.5 cc sterile, flint glass vials and the vials stoppered with rubber closures and sealed with aluminum shells.

EXAMPLE 3

An m-AMSA-L-pyroglutamate salt dosage form of the present invention was prepared by the following procedure:

Ten grams of m-AMSA base was dissolved in 85 ml of 1-methyl-2-pyrrolidinone.

One molar equivalent of L-pyroglutamic acid (3.281 g.) was then added and rapid stirring was continued to dissolve the L-pyroglutamic acid. The volume was then brought up to 100 ml with 1-methyl-2-pyrrolidinone and rapidly stirred for an additional ½ hour. The resulting solution contained 100 mg/ml of m-AMSA activity.

The solution was passed under a nitrogen atmosphere through a 0.22 micron pore size membrane filter using aseptic technique and the filtrate collected in a suitable sterile container.

Five ml portions of filtrate were placed in 8.5 cc sterile flint glass vials and the vials with rubber closures and sealed with aluminum shells.

EXAMPLE 4

An m-AMSA-L-pyroglutamate salt dosage form of the present invention was prepared by the following procedure:

Ten grams of m-AMSA base was dissolved in 85 ml of 1-methyl-2-pyrrolidinone.

Two molar equivalents of L-pyroglutamic acid (6.562 g.), were then added and rapid stirring was continued to dissolve the pyroglutamic acid. The volume was then brought up to 100 ml with 1-methyl-2-pyrrolidinone and rapidly stirred for an additional ½ hour. The resulting solution contained 100 mg/ml of m-AMSA activity.

The solution was passed under a nitrogen atmosphere through a 0.22 micron pore size membrane filter using aseptic technique and the filtrate collected in a suitable sterile container.

Ten ml portions of filtrate were placed in 17.5 cc sterile flint glass vials and the vials stopped with rubber closures and sealed with aluminum shells.

EXAMPLE 5

An m-AMSA-D,L-pyroglutamate salt dosage form of the present invention was prepared by the following procedure:

Ten grams of m-AMSA base was dissolved in 85 ml of 1-methyl-2-pyrrolidinone.

One molar equivalent of D,L-pyroglutamic acid (3.281 g.) was then added and rapid stirring was continued to dissolve the pyroglutamic acid. The volume was then brought up to 100 ml with 1-methyl-2-pyrrolidinone and rapidly stirred for an additional ½ hour. The resulting solution contained 100 mg/ml of m-AMSA activity.

The solution was passed under a nitrogen atmosphere through a 0.22 micron pore size membrane filter using aseptic technique and the filtrate collected in a suitable sterile container.

Ten ml portions of filtrate were placed in 17.5 cc sterile flint glass vials and the vials stopped with rubber closures and sealed with aluminum shells.

EXAMPLE 6

An m-AMSA-D,L-pyroglutamate salt dosage form of the present invention was prepared by the following procedure:

Ten grams of m-AMSA base was dissolved in 85 ml of 1-methyl-2-pyrrolidinone.

Two molar equivalents of D,L-pyroglutamic acid (6.562 g.), were then added and rapid stirring was continued to dissolve the pyroglutamic acid. The volume was then brought up to 100 ml with 1-methyl-2-pyrrolidinone and rapidly stirred for an additional ½ hour. The resulting solution contained 100 mg/ml of m-AMSA activity.

The solution was passed under a nitrogen atmosphere through a 0.22 micron pore size membrane filter using aseptic technique and the filtrate collected in a suitable sterile container.

Ten ml portions of filtrate were placed in 17.5 cc sterile flint glass vials and the vials stopped with rubber closures and sealed with aluminum shells.

EXAMPLE 7

An m-AMSA-L(+)-lactate-L-pyroglutamate salt dosage form of the present invention was prepared by the following procedure:

Ten grams of m-AMSA base was dissolved in 85 ml of 1-methyl-2-pyrrolidinone by rapid stirring.

One molar equivalent of L(+)-lactic acid (2.29 g.), plus one molar equivalent (3.28 g), of L-pyroglutamic acid was then added and rapid stirring was continued to dissolve the acid. The volume was then brought up to 100 ml with 1-methyl-2-pyrrolidinone and rapidly stirred for an additional ½ hour. The resulting solution contained 100 mg/ml of m-AMSA activity.

The solution was passed under a nitrogen atmosphere through a 0.22 micron pore size membrane filter using aseptic technique and the filtrate collected in a suitable sterile container.

Ten ml portions of filtrate were placed in 17.5 cc sterile flint glass vials and the vials stopped with rubber closures and sealed with aluminum shells.

EXAMPLE 8

An m-AMSA-L(+)-lactate-D,L-pyroglutamate dosage form of the present invention was prepared by the following procedure:

Ten grams of m-AMSA base was dissolved in 85 ml of 1-methyl-2-pyrrolidinone by rapid stirring.

One molar equivalent of L(+)-lactic acid (2.29 g.). plus one molar equivalent of D,L- pyroglutamic acid (3.28 g), was then added and rapid stirring was continued to dissolve the lactic acid. The volume was then brought up to 100 ml with 1-methyl-2-pyrrolidinone and rapidly stirred for an additional ½ hour. The resulting solution contained 100 mg/ml of m-AMSA activity.

The solution was passed under a nitrogen atmosphere through a 0.22 micron pore size membrane filter using aseptic technique and the filtrate collected in a suitable sterile container.

Ten ml portions of filtrate were placed in 17.5 cc sterile, flint glass vials and the vials stopped with rubber closures and sealed with aluminum shells.

What is claimed is:

1. A stable, concentrated solution of an acid-salt of m-AMSA selected from the group consisting of lactic acid salt, pyroglutamic acid salt and mixtures thereof containing from about 20 to 100 mg/ml of m-AMSA activity dissolved in 1-methyl-2-pyrrolidinone.

2. The solution of claim 1 wherein the acid-salt is the lactic acid salt.

3. The solution of claim 1 wherein the acid-salt is the L(+)-lactic acid salt.

4. The solution of claim 2 wherein the acid-salt is the D(−)-lactic acid salt.

5. The solution of claim 1 wherein the acid-salt is a pyroglutamic acid salt.

6. The solution of claim 5 wherein the acid-salt is the L-pyroglutamic acid salt.

7. The solution of claim 5 wherein the acid-salt is the D,L-pyroglutamic acid salt.

8. The solution of claim 1 wherein the acid salt is a mixture of the lactic acid and pyroglutamic acid salts.

9. The solution of claim 8 wherein the acid-salt is a mixture of the L(+)-lactic acid and the L-pyroglutamic acid salts.

10. The solution of claim 8 wherein the acid-salt is a mixture of the L(+)-lactic acid and the D,L-pyroglutamic acid salts.

11. The solution of claim 8 wherein the acid-salt is a mixture of the L(+)-lactic acid and the L-and D,L-pyroglutamic acid salts.

* * * * *